US012564549B2

(12) United States Patent (10) Patent No.: US 12,564,549 B2
Shima et al. (45) Date of Patent: Mar. 3, 2026

(54) CLEANSER COMPOSITION

(71) Applicant: Shiseido Company, Ltd., Tokyo (JP)

(72) Inventors: Takaaki Shima, Tokyo (JP); Yang Zhang, Tokyo (JP); Kei Watanabe, Tokyo (JP); Yuki Watanabe, Tokyo (JP); Kazuki Masuda, Tokyo (JP)

(73) Assignee: Shiseido Company, Ltd., Tokyo (JP)

( * ) Notice: Subject to any disclaimer, the term of this patent is extended or adjusted under 35 U.S.C. 154(b) by 554 days.

(21) Appl. No.: 17/924,090

(22) PCT Filed: Mar. 26, 2021

(86) PCT No.: PCT/JP2021/012800
§ 371 (c)(1),
(2) Date: Nov. 8, 2022

(87) PCT Pub. No.: WO2021/229928
PCT Pub. Date: Nov. 18, 2021

(65) Prior Publication Data
US 2023/0190626 A1 Jun. 22, 2023

(30) Foreign Application Priority Data
May 14, 2020 (JP) ................................. 2020-085107

(51) Int. Cl.
| | |
|---|---|
| *A61K 8/00* | (2006.01) |
| *A61K 8/02* | (2006.01) |
| *A61K 8/37* | (2006.01) |
| *A61K 8/86* | (2006.01) |
| *A61Q 19/10* | (2006.01) |

(52) U.S. Cl.
CPC .............. *A61K 8/86* (2013.01); *A61K 8/0208* (2013.01); *A61K 8/375* (2013.01); *A61Q 19/10* (2013.01)

(58) Field of Classification Search
None
See application file for complete search history.

(56) References Cited

U.S. PATENT DOCUMENTS

| | | |
|---|---|---|
| 10,231,920 B2 | 3/2019 | Yamada et al. |
| 2008/0188395 A1 | 8/2008 | Murase et al. |
| 2012/0073591 A1 | 3/2012 | Chen |

(Continued)

FOREIGN PATENT DOCUMENTS

| | | |
|---|---|---|
| EP | 1 952 795 A2 | 8/2008 |
| EP | 2 559 708 A1 | 2/2013 |

(Continued)

OTHER PUBLICATIONS

Cosme Labo, Japan, "Body Scrub," Mintel GNPD [online] Sep. 2019, ID#6859183, 2 pages.

(Continued)

*Primary Examiner* — Necholus Ogden, Jr.
(74) *Attorney, Agent, or Firm* — Foley & Lardner LLP

(57) ABSTRACT

A cleanser composition contains (A) a nonionic surfactant having a HLB of from 10 to 18; and (B) a cosurfactant including at least one selected from the group consisting of alkylglycerols and glycerin fatty acid esters. A content of the cosurfactant is 0.3% by mass or greater relative to the mass of the cleanser composition. A total amount of ionic surfactants is 0.10% by mass or less relative to the mass of the cleanser composition.

15 Claims, 1 Drawing Sheet

(56) References Cited

U.S. PATENT DOCUMENTS

| | | | |
|---|---|---|---|
| 2014/0142016 A1 | 5/2014 | Tomokuni et al. | |
| 2017/0151159 A1 | 6/2017 | Yamada et al. | |
| 2019/0091114 A1* | 3/2019 | Choi .................... A61K 8/44 |
| 2019/0247286 A1 | 8/2019 | Watanabe et al. | |
| 2020/0268628 A1 | 8/2020 | Hu et al. | |

FOREIGN PATENT DOCUMENTS

| | | |
|---|---|---|
| EP | 1 980 241 B1 | 10/2015 |
| JP | 2008-260822 A | 10/2008 |
| JP | 2010-070521 A | 4/2010 |
| JP | 2011-012252 A | 1/2011 |
| JP | 2012-214406 A | 11/2012 |
| JP | 2012-240962 A | 12/2012 |
| JP | 2013-032348 A | 2/2013 |
| JP | 5427970 B1 | 2/2014 |
| JP | 2014-091734 A | 5/2014 |
| JP | 2014-101285 A | 6/2014 |
| JP | 2014-181206 A | 9/2014 |
| JP | 2019-038792 A | 3/2019 |
| WO | WO-2011/129374 A1 | 10/2011 |
| WO | WO-2016090247 A1 * | 6/2016 ............ A61K 8/042 |
| WO | WO-2018/074149 A1 | 4/2018 |
| WO | WO-2018/180315 A1 | 10/2018 |

OTHER PUBLICATIONS

Watanabe et al., "Novel Vesicle and Sponge Phase Prepared in Amphoteric Surfactant/Anionic Surfactant/Oleic Acid/Water System," Langmuir, 2001, 17:7219-7224.
Asahi Group Foods, Japan, Cleansing Milk, ID# 7536999, Mintel GNPD [online], Apr. 2020, URL:https://portal.mintel.com, 4 pages.
Dr.Ci:Labo, Japan, White Cleansing Milk EX, ID# 5448563, Mintel GNPD [online], Feb. 2018, URL:https://portal.mintel.com, 5 pages.
Mandom, Japan, Baby Moist Cleansing Cream, ID# 1401323, Mintel GNPD [online], Aug. 2010, URL:https://portal.mintel.com, 3 pages.
Noevir, Japan, Cleansing Milk, ID# 6729393, Mintel GNPD [online], Jul. 2019, URL:https://portal.mintel.com, 3 pages.
Shiseido Liyuan Cosmetics, China, Collagen Cleansing Foam, ID#7081497, Mintel GNPD [online], Feb. 2020, URL:https://portal.mintel.com, 5 pages.

* cited by examiner

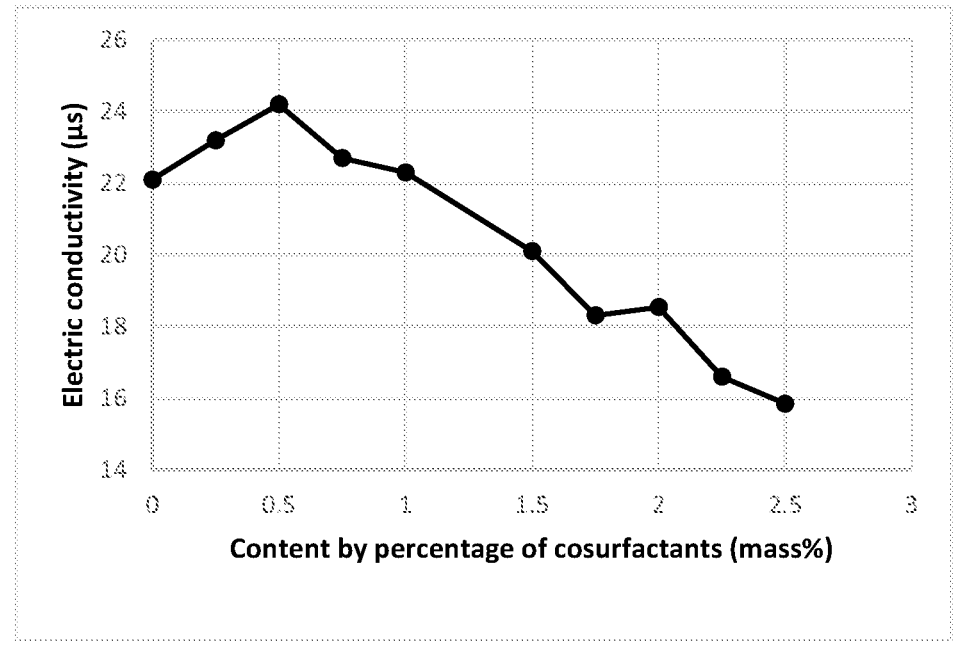

CLEANSER COMPOSITION

CROSS REFERENCE TO RELATED APPLICATIONS

The present application is the U.S. National Stage of PCT/JP2021/012800, filed Mar. 26, 2021, which is based upon and claims the benefit of priority from Japanese Patent Application No. 2020-085107 filed on May 14, 2020, the entire contents of which are incorporated herein by reference.

TECHNICAL FIELD

The present disclosure relates to a cleanser composition. For example, the present disclosure relates to a cleanser composition applicable to the skin.

BACKGROUND ART

Known examples of cleansers for removing cosmetics (makeup) from the skin include: rinse-off-type cleansers that, for example, cause cosmetics to lift up from the skin and be rinsed off together with the cleanser (see, for example, Patent Literature 1); and types of cleansers (leave-on-type or wipe-off-type cleansers) used to wipe off cosmetics on the skin and thus do not have to be rinsed off (see, for example, Patent Literature 2).

The cleansing composition disclosed in Patent Literature 1 contains (A) from 2 to 17.5% by mass of an anionic surfactant, (B) from 1 to 17.5% by mass of an amphoteric surfactant, (C) from 2.5 to 17% by mass of a hydrophilic nonionic surfactant, and (D) from 0.2 to 5% by mass of an oily component, wherein the cleansing composition contains no substantial amount of monoglycerin fatty acid ester or monoalkyl monoglyceryl ether including an alkyl group or acyl group having 9 or more carbon atoms, and contains no substantial amount of diglycerin fatty acid ester or monoalkyl diglyceryl ether including an alkyl group or acyl group having 8 or more carbon atoms.

Patent Literature 2 discloses an aqueous wipe-off cleansing cosmetic for removing makeup cosmetics. The cleansing cosmetic contains (A) from 3 to 10% by mass of a polyoxyethylene glyceryl fatty acid ester, (B) from 0.005 to 2% by mass of an amphoteric surfactant, and (C) from 1 to 12% by mass of a polyol, and substantially contains no anionic surfactant and no cationic surfactant.

Non-Patent Literature 1 discloses a composition having a "sponge phase" constituted by an amphoteric surfactant, an anionic surfactant, oleic acid, and water.

CITATION LIST

Patent Literature

Patent Literature 1: WO 2018/074149
Patent Literature 2: Japanese Patent No. 5427970
Non-Patent Literature 1: Kei Watanabe et al., "Novel Vesicle and Sponge Phase Prepared in Amphoteric Surfactant/Anionic Surfactant/Oleic Acid/Water System", American Chemical Society, Langmuir, 2001, Vol. 17, pp. 7219-7224

SUMMARY OF INVENTION

Technical Problem

The following analysis can be made from the perspective of the present disclosure.

Rinse-off-type cleansers, such as those disclosed in Patent Literature 1, may cause strong irritation to the skin, and hence, it is not preferable to leave such cleansers on the skin. The cleansing cosmetic disclosed in Patent Literature 2 is a leave-on-type cosmetic, but contains an amphoteric surfactant; if the amphoteric surfactant remains on the skin after wiping, it may cause irritation to the skin. The composition having a sponge phase as disclosed in Non-Patent Literature 1 is thought to have high cleansability. Unfortunately, this composition also contains an amphoteric surfactant, which may cause irritation to the skin if it remains on the skin.

Hence, there is a demand for a cleanser composition having high cleansability while being less irritable to the skin.

Solution to Problem

According to a first aspect of the present disclosure, a cleanser composition is provided, the composition containing (A) a nonionic surfactant having a HLB of from 10 to 18, and (B) a cosurfactant including at least one selected from the group consisting of alkylglycerols and glycerin fatty acid esters. A content of the cosurfactant is 0.3% by mass or greater relative to the mass of the cleanser composition. A total amount of ionic surfactants is 0.1% by mass or less relative to the mass of the cleanser composition.

According to a second aspect of the present disclosure, a cleanser composition is provided, the composition containing (A) at least two types of nonionic surfactants respectively having different HLBs, and (B) a cosurfactant including at least one selected from the group consisting of alkylglycerols and glycerin fatty acid esters. A content of the cosurfactant is 0.3% by mass or greater relative to the mass of the cleanser composition. A total amount of ionic surfactants is 0.1% by mass or less relative to the mass of the cleanser composition.

According to a third aspect of the present disclosure, A cleanser composition is provided, the composition containing a nonionic surfactant having a HLB of 8 or greater. The cleanser composition has a sponge phase including the nonionic surfactant as a constituent component. A total amount of ionic surfactants is 0.1% by mass or less relative to the mass of the cleanser composition.

Advantageous Effects of Invention

The cleanser composition of the present disclosure is less irritable to the skin and has high cleansing capability. Thus, the cleanser composition of the present disclosure can be used, for example, as a cleanser for application to the skin.

BRIEF DESCRIPTION OF DRAWINGS

FIG. 1 is a graph showing changes in electric conductivity with respect to the content by percentage of the cosurfactants in Test Examples 1.

DESCRIPTION OF EMBODIMENTS

Preferred modes of the aforementioned aspects will be described below.

According to a preferred mode of the aforementioned second aspect, the nonionic surfactant has a HLB of from 10 to 14. A content of the nonionic surfactant is 1% by mass or greater relative to the mass of the cleanser composition.

According to a preferred mode of the aforementioned second aspect, the nonionic surfactants have a weighted average HLB of from 10 to 18.

According to a preferred mode of the aforementioned second aspect, a total amount of the cosurfactant is from 0.1 to 0.9 parts by mass relative to 1 part by mass of the nonionic surfactants.

According to a preferred mode of the aforementioned first and second aspects, the cleanser composition has a sponge phase including the nonionic surfactant(s) and the cosurfactant as constituent components.

According to a preferred mode of the aforementioned third aspect, the cleanser composition further comprises a cosurfactant including at least one selected from the group consisting of alkylglycerols and glycerin fatty acid esters. A content of the cosurfactant is 0.3% by mass or greater relative to the mass of the cleanser composition.

According to a preferred mode of the aforementioned third aspect, the nonionic surfactant has a HLB of from 10 to 14. A content of the nonionic surfactant is 1% by mass or greater relative to the mass of the cleanser composition.

According to a preferred mode of the aforementioned third aspect, the nonionic surfactant includes at least two types of nonionic surfactants respectively having different HLBs. The nonionic surfactants have a weighted average HLB of from 10 to 18.

According to a preferred mode of the aforementioned third aspect, the cleanser composition further comprises a cosurfactant including at least one selected from the group consisting of alkylglycerols and glycerin fatty acid esters. A content of the cosurfactant is 0.3% by mass or greater relative to the mass of the cleanser composition.

According to a preferred mode of the aforementioned third aspect, a total amount of the cosurfactant is from 0.1 to 0.9 parts by mass relative to 1 part by mass of the nonionic surfactants.

According to a preferred mode of the aforementioned second and third aspects, the nonionic surfactants include a first nonionic surfactant having a HLB of 14 or greater, and a second nonionic surfactant having a HLB of from 6 to 13.

According to a preferred mode of the aforementioned second and third aspects, a content of the first nonionic surfactant is from 0.5 to 50% by mass relative to the mass of the cleanser composition. A content of the second nonionic surfactant is from 0.02 to 3% by mass relative to the mass of the cleanser composition.

According to a preferred mode of the aforementioned first to third aspects, the alkylglycerol is ethylhexylglycerin.

According to a preferred mode of the aforementioned first to third aspects, the nonionic surfactant is a polyoxyalkylene glycerin fatty acid ester.

According to a preferred mode of the aforementioned first to third aspects, a content of an oily component is 1% by mass or less relative to the mass of the cleanser composition.

According to a preferred mode of the aforementioned first to third aspects, the cleanser composition further comprises 70% by mass or greater of water relative to the mass of the cleanser composition.

According to a preferred mode of the aforementioned first to third aspects, the cleanser composition is applicable to cleansing of a cosmetic.

According to a preferred mode of the aforementioned first to third aspects, the cleanser composition is usable as a leave-on-type or wipe-off-type composition.

A cleanser composition according to a first embodiment of the present invention will be described. The cleanser composition of the present disclosure is applicable, for example, to cleansing of the skin. Particularly, the cleanser composition of the present disclosure is applicable to cleansing of cosmetics (makeup) on the skin.

In the present disclosure, "substantial amount" refers to an amount capable of bringing about the functions/effects achieved by the addition of the compound in question.

In the following description, POE is an acronym of polyoxyethylene, POP is an acronym of polyoxypropylene, and the number in parentheses after POE or POP indicates the average number of moles of POE groups or POP groups added in the compound in question.

A cleanser composition according to a first embodiment of the present disclosure will be described. The cleanser composition according to the first embodiment contains a plurality of nonionic surfactants respectively having different HLBs. For example, the nonionic surfactants may include a first nonionic surfactant, and a second nonionic surfactant having a HLB lower than that of the first nonionic surfactant. Three or more types of nonionic surfactants may be included.

In the first embodiment, the weighted average HLB of the plurality of nonionic surfactants is preferably 10 or greater, more preferably 12 or greater. The weighted average HLB of the plurality of nonionic surfactant is preferably 18 or less, more preferably 16 or less. For example, the first nonionic surfactant may have a HLB of 14 or greater, or a HLB of 15 or greater. The second nonionic surfactant may have a HLB of from 6 to 13. "Weighted average HLB" as referred to in the present disclosure refers to the average value of HLBs, calculated with consideration given to the mass ratio of the nonionic surfactants. For example, a mixture containing 20 g of a first surfactant having a HLB of 14 and 80 g of a second surfactant having a HLB of 10 will have a weighted average HLB of 13.2 (=(HLB 14×80 g+HLB 10×20 g)/(80 g+20 g)). By setting the weighted average HLB in this way, it is possible to form a sponge phase, as will be described further below.

The first nonionic surfactant and the second nonionic surfactant may each be a polyoxyalkylene glycerin fatty acid ester. For the first nonionic surfactant, it is possible to use, for example, PEG-60 glyceryl isostearate having a HLB of 16, etc. For the second nonionic surfactant, it is possible to use, for example, PEG-20 glyceryl triisostearate having a HLB of 8, PEG-8 glyceryl isostearate having a HLB of 10, PEG-7 glyceryl cocoate having a HLB of 13, PEG-15 glyceryl isostearate having a HLB of 12, etc.

Examples of the hydrophilic nonionic surfactants that may be used may include POE sorbitan fatty acid ester (such as POE sorbitan monooleate, POE sorbitan monostearate, POE sorbitan monooleate, POE sorbitan tetraoleate); POE sorbit fatty acid ester (such as POE sorbit monolaurate, POE sorbit monooleate, POE sorbit pentaoleate, POE sorbit monostearate), POE glyceryl fatty acid ester (such as POE monooleate such as POE glyceryl monostearate, POE glyceryl monoisostearate, POE glyceryl triisostearate); POE fatty acid ester (such as POE distearate, POE monodioleate, ethyleneglycol distearate); POE alkyl ether (such as POE lauryl ether, POE oleyl ether, POE stearyl ether, POE behenyl ether, POE-2-octyldodecyl ether, POE cholestanol ether); puluronic type (such as Puluronic), POE/POP alkyl ethers (such as POE/POP cetyl ether, POE/POP 2-decyltetradecyl ether, POE/POP monobutyl ether, POE/POP hydrogenated lanoline, POE/POP glycerin ether); tetra POE/tetra POP ethylenediamine condensation products (such as Tetronic); POE castor oil hydrogenated castor oil derivative (such as POE caster oil, POE hydrogenated caster oil, POE hydrogenated caster oil monoisostearate, POE hydrogenated castor oil triisostearate, POE hydrogenated caster oil mono-pyroglutamate monoisostearate diester, POE hydrogenated oil maleate); POE beeswax/lanoline derivative (such as POE sorbitol beeswax); alkanolamide (such as coconut oil fatty acid diethanolamide, lauric acid monoethanolamide, fatty acid isopropanolamide); POE propyleneglycol fatty acid ester; POE alkyl amines; POE fatty acid amide; sucrose fatty acid ester; alkylethoxydimethylamine oxide; trioleyl phosphoric acid and the like.

The content by percentage of the first nonionic surfactant relative to the mass of the cleanser composition may be 0.5% by mass or greater, 0.8% by mass or greater, 1% by mass or greater, 1.2% by mass or greater, or 1.5% by mass or greater. The content by percentage of the first nonionic surfactant relative to the mass of the cleanser composition may be 5% by mass or less, 4.5% by mass or less, 3.5% by mass or less, or 3% by mass or less.

The content by percentage of the second nonionic surfactant relative to the mass of the cleanser composition may be 0.02% by mass or greater, 0.05% by mass or greater, 0.1% by mass or greater, or 0.2% by mass or greater. The content by percentage of the second nonionic surfactant relative to the mass of the cleanser composition may be 3% by mass or less, 2.5% by mass or less, 2% by mass or less, 1.5% by mass or less, 1% by mass or less, 0.8% by mass or less, or 0.5% by mass or less.

The cleanser composition according to the first embodiment is thought to have a sponge phase including the nonionic surfactants and a cosurfactant as constituent components. The sponge phase will be described further below.

The cleanser composition according to the first embodiment may further contain a cosurfactant. "Cosurfactant" as referred to in the present disclosure is a substance that cannot form an assembly in a solvent by itself, but can form an interfacial membrane together with the nonionic surfactant(s) and change the properties of the interfacial membrane of the nonionic surfactant(s). In the present disclosure, the cosurfactant contributes to the sponge phase formation by the nonionic surfactant(s).

The cosurfactant may include, for example, at least one component selected from the group consisting of alkylglycerols and glycerin fatty acid esters. An example of the alkylglycerol may include ethylhexylglycerin. "Glycerin fatty acid esters" as referred to in the present disclosure may include polyglycerin fatty acid esters. Examples of the glycerin fatty acid esters may include polyglyceryl-2 laurate, polyglyceryl-2 caprate, etc.

The content by percentage of the cosurfactant relative to the mass of the cleanser composition is preferably 0.3% by mass or greater, more preferably 0.4% by mass or greater, even more preferably 0.5% by mass or greater. The content of the cosurfactant relative to the mass of the cleanser composition may be 1% by mass or greater, 1.5% by mass or greater, or 2% by mass or greater. The content by percentage of the cosurfactant relative to the mass of the cleanser composition may be 25% by mass or less, 20% by mass or less, 15% by mass or less, 10% by mass or less, 5% by mass or less, 4% by mass or less, 3.5% by mass or less, 3% by mass or less, 2.5% by mass or less, 2% by mass or less, 1.5% by mass or less, 1% by mass or less, or 0.8% by mass or less.

As regards the mass ratio between the cosurfactant and the nonionic surfactants, the total amount of the cosurfactant relative to 1 part by mass of the nonionic surfactants (total amount) is preferably 0.1 parts by mass or greater. If the content of the cosurfactant is less than 0.1 parts by mass, it is difficult to form a sponge phase. The total amount of the cosurfactant relative to 1 part by mass of the nonionic surfactants (total amount) may be 0.3 parts by mass or greater, or 0.5 parts by mass or greater. The total amount of the cosurfactant relative to 1 part by mass of the nonionic surfactants may be 0.9 parts by mass or less, or 0.7 parts by mass or less.

A cleanser composition according to a second embodiment of the present disclosure will be described. The cleanser composition according to the first embodiment contains a plurality of types of nonionic surfactants, whereas the cleanser composition according to the second embodiment may contain at least one type of nonionic surfactant. The cleanser composition according to the second embodiment contains at least one type of nonionic surfactant and a cosurfactant.

In the second embodiment, the HLB of the nonionic surfactant is preferably 10 or greater. The HLB of the nonionic surfactant is preferably 18 or less, more preferably 16 or less, even more preferably 14 or less.

The content by percentage of the nonionic surfactant relative to the mass of the cleanser composition may be 0.5% by mass or greater, or 1% by mass or greater. The content by percentage of the nonionic surfactant relative to the mass of the cleanser composition may be 5% by mass or less, 4% by mass or less, or 3% by mass or less.

The content by percentage of the cosurfactant relative to the mass of the cleanser composition is preferably 0.3% by mass or greater. The content of the cosurfactant relative to the mass of the cleanser composition may be 0.5% by mass or greater, 1% by mass or greater, 1.5% by mass or greater, or 2.5% by mass or greater. If the content of the cosurfactant is less than 0.3% by mass, it is difficult to form a sponge phase. The content by percentage of the cosurfactant relative to the mass of the cleanser composition may be 50% by mass or less, 40% by mass or less, 30% by mass or less, 20% by mass or less, 10% by mass or less, 5% by mass or less, 4% by mass or less, or 3% by mass or less.

The total amount of the cosurfactant relative to 1 part by mass of the nonionic surfactant(s) (total amount) may be 0.1 parts by mass or greater, or 0.2 parts by mass or greater. The total amount of the cosurfactant relative to 1 part by mass of the nonionic surfactant(s) (total amount) may be 3 parts by mass or less, or 2.5 parts by mass or less.

The cleanser composition according to the second embodiment is thought to have a sponge phase including the nonionic surfactant(s) and cosurfactant as constituent components. The sponge phase will be described further below.

Aspects of the second embodiment other than those described above may be the same as those of the first embodiment. For aspects other than those described above, the description of the first embodiment is incorporated by reference, and description thereof is omitted herefrom.

A cleanser composition according to a third embodiment of the present disclosure will be described. The cleanser composition according to the third embodiment has a sponge phase including a nonionic surfactant as a constituent component. "Sponge phase" as referred to in the present disclosure is a phase or state in which surfactant molecules assemble together endlessly in water to form a continuous assembly, with water being retained between the hydrophilic groups of the continuous assembly. The form of water is random and has no regularity. The lipophilic group of a surfactant molecule is arranged facing the lipophilic group of another surfactant molecule. Hence, the sponge phase can also be defined as a phase or state in which surfactant bilayer membranes partition water, to form minuscule domains of water.

The nonionic surfactant is the same as the nonionic surfactants of the first and second embodiments. As regards the nonionic surfactant, the description of the first and second embodiments is incorporated by reference, and description thereof is omitted herefrom.

The cleanser composition according to the third embodiment of the present disclosure may further contain a cosurfactant. The cosurfactant is thought to constitute the sponge phase together with the nonionic surfactant. The cosurfactant is the same as the cosurfactant of the first and second embodiments. As regards the cosurfactant, the description of the first and second embodiments is incorporated by reference, and description thereof is omitted herefrom.

The presence of a sponge phase can be verified by electric conductivity measurement. For example, various mixed solutions including a nonionic surfactant and a cosurfactant are prepared by changing the concentration of the cosurfactant stepwise while keeping the concentration of the nonionic surfactant constant, and the electric conductivity of each solution is measured. A graph is rendered by plotting the electric conductivity against the concentration of the cosurfactant. In the graph, if there is a region wherein the electric conductivity decreases as the concentration of the cosurfactant increases, it can be deemed that a sponge phase has been formed in that region.

A sponge phase is created by adding a cosurfactant substance to a micellar aqueous solution. Due to the creation of the sponge phase, the bilayer membrane of the surfactant forms a network structure in water. This restricts the range in which ions can move, thus resulting in a drop in electric conductivity. Hence, it can be said that the compositional make-up at which the electric conductivity starts to drop is the concentration at which a sponge phase starts to form.

The presence of a sponge phase can also be verified by observation with a transmission electron microscope using a frozen replica membrane (i.e., electron microscope observation of a phase sample prepared by the freeze-fracture technique) (see, for example, T. Imae, T. Iwamoto, G. Platz, C. Thunig, Colloid polym. Sci., 272, 604-611 (1994)).

Preferred modes of the cleanser compositions according to the first to third embodiments of the present disclosure will be described below.

Preferably, the cleanser composition of the present disclosure is an aqueous composition.

The cleanser composition of the present disclosure may further contain water. Examples of water that may be used include water used in such products as cosmetics, quasi-pharmaceutical products, etc., with usable examples including purified water, ion-exchanged water, tap water, etc.

The content by percentage of water relative to the mass of the cleanser composition may be, for example, 60% by mass or greater, 65% by mass or greater, 70% by mass or greater, 75% by mass or greater, or 80% by mass or greater. The content by percentage of water relative to the mass of the cleanser composition may be, for example, 95% by mass or less, 90% by mass or less, 85% by mass or less, or 80% by mass or less.

In the cleanser composition of the present disclosure, it is preferred that the content of oily component(s) relative to the mass of the cleanser composition is preferably 1% by mass or less, more preferably 0.5% by mass or less, and it is also preferred that substantially no oily component is contained in the cleanser composition. If the content of oily component(s) exceeds 1% by mass, the user is likely to feel greasiness after cleansing.

In the cleanser composition of the present disclosure, the content by percentage of ionic surfactant(s) relative to the mass of the cleanser composition is preferably 0.1% by mass or less, more preferably 0.05% by mass or less, more preferably 0.01% by mass or less, more preferably less than 0.005% by mass, and it is even more preferred that substantially no ionic surfactant is contained. The inclusion of an ionic surfactant may increase irritation to the skin when the composition remains on the skin after use. Examples of ionic surfactants include anionic surfactants, cationic surfactants, and amphoteric surfactants.

The cleanser composition of the present disclosure is applicable to skin cleansers. For example, the cleanser composition of the present disclosure is applicable to cleansers for removing cosmetics (makeup). Particularly, the cleansing composition, which has a sponge phase, has high cleansing capability even without containing any oily component. For example, the cleanser composition of the present disclosure is applicable to the removal of waterproof-type cosmetics applied to the skin. Also, the cleanser composition of the present disclosure can be used to wipe off and remove dirt/stains.

The cleanser composition of the present disclosure has a low content by percentage of ionic surfactant(s). Hence, irritation to the skin can be suppressed. Further, the cleanser composition of the present disclosure can be used as a leave-on-type or wipe-off-type composition that does not have to be rinsed off with water after wiping.

In the cleanser composition of the present disclosure, the content of oily component(s) can be minimized. Hence, greasiness after use can be suppressed, and the user can obtain a fresh feel upon use.

The cleanser composition having a sponge phase has a transparent (including translucent) appearance. The cleanser composition of the present disclosure can exhibit a favorable appearance.

If necessary, the cleansing composition of the present disclosure may contain other components as appropriate, such as water-soluble alcohols, alkylene oxide derivatives, moisturizers, water-soluble polymers, thickeners, film-forming agents, UV absorbers, metal ion sequestering agents, amino acids, organic amines, polymer emulsions, pH adjusters, skin nutrients, vitamins, antioxidants, antioxidant aids, perfumes, etc., in amounts that do not inhibit the effects of the present disclosure.

Examples of water-soluble alcohols may include at least one type selected from lower alcohols, polyhydric alcohols, polyhydric alcohol polymers, dihydric alcohol alkyl ethers, dihydric alcohol alkyl ethers, dihydric alcohol ether esters, glycerin monoalkyl ethers, sugar alcohols, monosaccharides, oligosaccharides, polysaccharides, and derivatives of the above.

Examples of the lower alcohol may include ethanol, propanol, isopropanol, isobutyl alcohol, t-butyl alcohol, and the like.

Examples of the polyhydric alcohol may include dihydric alcohol (such as ethylene glycol, propylen glycol, trimethylene glycol, 1,2-butylene glycol, 1,3-butylene glycol, tetramethylene glycol, 2,3-butylene glycol, pentamethylene glycol, 2-butene-1,4-diol, hexylene glycol, octylene glycol, etc); trihydric alcohol (such as glycerin, trimethylolpropane, etc); tetrahydric alcohol (such as such as pentaerythritol such as 1,2,6-hexanetriol, etc); pentahydric alcohol (such as xylitol, etc); hexahydric alcohol (such as sorbitol, mannitol, etc); polyhydric alcohol polymer (such as diethylene glycol, dipropylene glycol, triethylene glycol, polypropylene glycol, tetraethylene glycol, diglycerin, polyethylene glycol, triglycerin, tetraglycerin, polyglycerin, etc); dihydric alcohol alkyl ethers (such as ethylene glycol monomethyl ether, ethylene glycol monoethyl ether, ethylene glycol monobutyl ether, ethylene glycol monomphenyl ether, ethylene glycol monohexyl ether, ethylene glycol mono2-methylhexyl ether, ethylene glycol isoamyl ether, ethylene glycol benzil ether, ethylene glycol isopropyl ether, ethylene glycol dimethyl ether, ethylene glycol diethyl ether, ethylene glycol dibutyl ether, etc); dihydric alcohol alkyl ethers (such as diethylene glycol monomethyl ether, diethylene glycol monoethyl ether, diethylene glycol monombutyl ether, diethylene glycol dimethyl ether, diethylene glycol diethyl ether, diethylene glycol butyl ether, diethylene glycol methylethyl ether, triethylene glycol monomethyl ether, triethylene glycol monoethyl ether, propylene glycol monomethyl ether, propylene glycol monoethyl ether, propylene glycol monobutyl ether, propylene glycol isopropyl ether, dipropylene glycol methyl ether, dipropylene glycol ethyl ether, dipropylene glycol butyl ether, etc); dihydric alcohol ether ethers (such as ethylene glycol monomethyl ether acetate, ethylene glycol monoethyl ether acetate, ethylene glycol monobutyl ether acetate, ethylene glycol monophenyl ether acetate, ethylene glycol diadipate, ethylene glycol disaccinate, diethylene glycol monoethyl ether acetate, diethylene glycol monobutyl ether acetate, propylene glycol monomethyl ether acetate, propylene glycol monoethyl ether acetate, propylene glycol monopropyl ether acetate, propylene glycol monophenyl ether acetate, etc); glycerin monoalkyl ether (such as chimyl alcohol, selachyl alcohol, batyl alcohol, etc); sugar alcohol (such as sorbitol, maltitol, maltotriose, mannitol, sucrose, erythritol, glucose, fructose, starch sugar, maltose, xylitol, starch sugar hydrogenated alcohol, etc); glycolide, tetrahydrofurfuryl alcohol; POE-tetrahydrofurfuryl alcohol; POP/POE-butyl ether; tripolyoxypropylene glycerin ether; POP-glycerin ether; POP-glycerin ether phosphoric acid; POP/POE-pentaerythritol ether; polyglycerin, and the like.

Examples of the monosaccharides may include at least one selected from triose (such as D-glyceryl aldehyde, dihydroxyacetone, etc); tetrose (such as D-erythrose, D-erythrulose, D-threose, erythritol, etc); pentaose (such as L-arabinose, D-xylose, L-lyxose, D-arabinose, D-ribose, D-ribulose, D-xylulose, L-xylulose, etc); hexalose (such as D-glucose, D-talose, D-psicose, D-galactose, D-fructose, L-galactose, L-mannose, D-tagatose, etc); heptose (such as aldoheptose, heptulose, etc); octose (such as octulose, etc); deoxy sugar (such as 2-deoxy-D-ribose, 6-deoxy-L-galactose, 6-deoxy-L-mannose, etc); amino sugar (such as D-glucosamine, D-galactosamine, sialic acid, amino uronic acid, muramic acid, etc); uronic acid (such as D-grucuronic acid, D-mannuronic acid, L-guluronic acid, D-garacturonic acid, L-iduronic acid, etc) and the like.

Examples of the oligosaccharide may include at least one selected from sucrose, guntianose, umbelliferose, lactose, planteose, isolignoses, α,α-trehalose, raffinose, lignoses, umbilicin, stachyose, verbascoses, and the like.

Examples of the polysaccharide may include at least one selected from cellulose, quince seed, chondroitinsulfate, starch, galactan, dermatan sulfate, glycogen, acasia gum, heparansulfate, hyaluronan, gum tragacanth, keratan sulfate, chondoroitin, xanthan gum, mucoitin sulfate, guar gum, dextran, keratosulfate, locust bean gum, succinoglycan, caronic acid, and the like.

Examples of other polyols may include at least one polyol selected from polyoxyethylene methyl glucoside (Glucam E-10) and polyoxypropylene methyl glucoside (Glucam P-10).

For the alkylene oxide derivative, it is possible to use any compound represented by the following Chem. 1. In the chemical formula represented by Chem. 1, AO represents a C3 to C4 oxyalkylene group, and preferably oxypropylene. EO represents an oxyethylene group. The letters m and n each represent the average number of moles of C3 to C4 oxyalkylene groups or oxyethylene groups added, respectively. Here, m is preferably 1 or greater, more preferably 5 or greater. m is preferably 70 or less, more preferably 45 or less. Further, n is preferably 1 or greater, more preferably 12 or greater. n is preferably 70 or less, more preferably 40 or less. The total of m and n is preferably 10 or greater, more preferably 20 or greater, even more preferably 30 or greater. The total of m and n is preferably 120 or less, more preferably 100 or less, even more preferably 80 or less. The percentage of oxyethylene groups relative to the total of oxyalkylene groups and oxyethylene groups is preferably from 20 to 80% by mass. The oxyalkylene groups and oxyethylene groups may be added in blocks or may be added randomly. $R^1$ and $R^2$ each represent a hydrogen atom or a C1 to C4 hydrocarbon group, which may be the same or different from one another. The rate of the number of hydrogen atoms to the number of hydrocarbon groups in $R^1$ and $R^2$ is preferably 0.15 or less. Preferably, $R^1$ and $R^2$ each represent a methyl group.

[Chem. 1]

$$R^1O{-}\left[(AO)_m(EO)_n\right]{-}R^2$$

The powder is not particularly limited so long as it is generally usable for cosmetic purposes, for example. Examples of the powder may include inorganic powder (such as talc, kaolin, mica, sericite, muscovite, phlogopite, synthetic mica, lepidolite, biotite, vermiculite, magnesium carbonate, calcium carbonate, aluminum silicate, barium silicate, calcium silicate, magnesium silicate, strontium silicate, tungstate, magnesium, silica, zeolite, glass, barium sulfate, calcined calcium sulfate (calcined gypsum), calcium phosphate, fluorine apatite, hydroxyapatite, ceramic powder, metallic soap (such as zinc myristate, calcium palimitate, and aluminum stearate), and boron nitride, etc); organic powder (such as polyamide resin powder (nylon powder), polyethylene powder, polymethylmethacrylate powder, polystyrene powder, styrene-acrylic acid copolymer powder, benzoguanamine resin powder, poly(tetrafluroethylene) powder, and cellulose powder, silicone resin powder, silk powder, wool powder, urethane powder, etc); inorganic white family pigment (such as titanium dioxide, zinc oxide, etc); inorganic red family pigment (such as iron oxide (colcothar), iron titanate, etc); inorganic brown family pigment (such as γ-iron oxide, etc); inorganic yellow family pigment (such as yellow iron oxide, loess, etc); inorganic black family pigment (such as black iron oxide, carbon black, lower titanium oxide, etc); inorganic purple family pigment (such as manganese violet, cobalt violet, etc); inorganic green family pigment (such as chrome oxide, chrome hydroxide, cobalt titanate, etc); inorganic blue family pigment (such as ultramarine, iron blue, etc); pearl pigment (such as titanium oxide coated mica, titanium oxide coated bismuth oxychloride, titanium oxide coated talc, colored titanium oxide coated mica, bismuth oxychloride, argentine, etc); metal powder pigment (such as aluminum powder, copper powder, etc); organic pigment such as zirconium, barium, or aluminum lake (such as organic pigment such as Red No. 201, Red No. 202, Red No. 204, Red No. 205, Red No. 220, Red No. 226, Red No. 228, Red No. 405, Red No. 201, Orange No. 203, Orange No. 204, Yellow No. 205, Yellow No. 401, Blue No. 401, Red No. 3, Red No. 104, Red No. 106, Red No. 227, Red No. 230, Red No. 401, Red No. 505, Orange No. 205, Yellow No. 4, Yellow No. 5, Yellow No. 202, Yellow No. 203, Green No. 3, and Blue No. 1, etc); natural pigment (such as chlorophyll, β-carotene, etc); and the like.

Examples of the moisturizers may include chondroitin sulfate, hyaluronic acid, mucoitin sulfate, charonic acid, atelocollagen, cholesteryl 12-hydroxystearate, sodium lactate, bile salt, dl-pyrrolidone carboxylate, alkyleneoxide derivative, short-chain soluble collagen, diglycerin (EO)PO adduct, chestnut rose extract, yarrow extract, melilot extract, and the like.

Examples of the natural water-soluble polymer may include plant-based polymer (such as gum Arabic, gum tragacanth, galactan, guar gum, locust bean gum, gum karaya, carrageenan, pectine, agar, quince seed (Cydonia oblonga), algae colloid (brown algae extract), starch (rice, corn, potato, wheat), glicyrrhizic acid); microorganism based polymer (such as xanthan gum, dextran, succinoglycan, pullulan, etc), animal-based polymer (such as collagen, casein, albumin, gelatine, etc) and the like.

Examples of the semisynthetic water-soluble polymer may include starch-based polymer (such as carboxymethyl starch, methylhydroxypropyl starch, etc); cellulose-based polymer (such as methylcellulose, ethylcellulose, methylhydroxypropylcellulose, hydroxyethylcellulose, cellulose sodium sulfate, hydroxypropylcellulose, carboxymethylcellulose, sodium calboxymethyl cellulose, crystalline cellulose, cellulose powder, etc); algin acid-based polymer (such as sodium alginate, propylene glycol alginate ester, etc), and the like.

Examples of the synthetic water-soluble polymer may include vinyl based polymer (such as polyvinyl alcohol, polyvinyl methyl ether, polyvinylpyrrolidone, carboxyvinylpolymer, etc); polyoxyethylene based polymer (such as polyoxyethylenepolyoxypropylene copolymer such as polyethylene glycol 20,000, 40,000 and 60,000, etc); acrylic polymer (such as sodium polyacrylate, polyethylacrylate, polyacrylamide, etc); polyethyleneimine; cationic polymer; and the like.

Examples of the thickeners may include gum arabic, carrageenan, karaya gum, tragacanth gum, carob gum, quince seed (marmelo), casein, dextrin, gelatin, sodium pectate, sodium alginate, methyl cellulose, ethyl cellulose, carboxymethyl cellulose (CMC), hydroxyethyl cellulose, hydroxypropyl cellulose, polyvinyl alcohol (PVA), polyvinylmethyl ether (PVM), PVP (polyvinyl pyrrolidone), polysodium acrylate, carboxyvinyl polymer, locust bean gum, guar gum, tamarind gum, dialkyldimethylammonium sulfate cellulose, xanthan gum, aluminum magnesium silicate, bentonite, hectorite, aluminum magnesium silicate (Veegum), sodium magnesium silicate (Laponite), silicic acid anhydride, taurate-based synthetic polymers, and acrylate-based synthetic polymers.

Examples of the film-forming agent may include an anionic film-forming agent (such as (meta)acrylic acid/(meta)acrylic acid ester copolymer, methyl vinyl ether/maleic anhydride copolymer, etc), a cationic film-forming agent (such as cationic cellulose, diallyldimethylammonium chloride polymer, diallyldimethylammonium chloride/acrylic amide copolymer, etc), a nonionc film-forming agent (such as polyvinyl alcohol, polyvinylpyrrolidone, polyvinyl acetate, polyacrylic ester copolymer, (meta)acrylamide, polymeric silicone, silicone resin, trimethylsiloxysilicate, etc), and the like.

Examples of the ultraviolet light absorbers may include benzoic acid family ultraviolet light absorber (such as p-aminobenzoic acid (hereinafter abbreviated as PABA), PABA monoglycerine ester, N,N-dipropoxy PABA ethyl ester, N,N-diethoxy PABA ethyl ester, N,N-dimethyl PABA ethyl ester, N,N-dimethyl PABA butyl ester, N,N-dimethyl PABA ethyl ester, etc); anthranilic acid family ultraviolet light absorber (such as homomenthyl N-acetylanthranilate etc); salicylic acid family ultraviolet light absorber (such as amyl salicylate, menthyl salicylate, homomenthyl salicylate, octyl salicylate, phenyl salicylate, benzyl salicylate, p-isopropanolphenyl salicylate, etc); cinnamic acid family ultraviolet light absorber (such as octyl methoxycinnamate, ethyl 4-isopropylcinnamate, methyl 2,5-diisopropylcinnamate, ethyl 2,4-diisopropylcinnamate, methyl 2,4-diisopropylcinnamate, propyl p-methoxycinnamate, isopropyl p-methoxycinnamate, isoamyl p-methoxycinnamate, octyl p-methoxycinnamate (2-ethylhexyl p-methoxycinnamate), 2-ethoxyethyl p-methoxycinnamate, cyclohexyl p-methoxycinnamate, ethyl α-cyano-β-phenylcinnamate, 2-ethylhexyl α-cyano-β-phenylcinnamate, glyceryl mono-2-ethyl-hexanoyl-diparamethoxy cinnamate, etc); benzophenone family ultraviolet light absorber (such as 2,4-dihydroxybenzophenone, 2,2'-dihydroxy-4-methoxybenzophenone, 2,2'-dihydroxy-4,4'-dimethoxybenzophenone, 2,2',4,4'-tetrahydroxybenzophenone, 2-hydroxy-4-methoxybenzophenone, 2-hydroxy-4-methoxy-4'-methylbenzophenone, 2-hydroxy-4-methoxybenzophenone-5-sulfonate, 4-phenylbenzophenone, 2-ethylhexyl-4'-phenyl-benzophenone-2-carboxylate, 2-hydroxy-4-n-octoxybenzophenone, 4-hydroxy-3-carboxybenzophenone, etc); 3-(4'-methylbenzylidene)-d,l-camphor and 3-benzylidene-d,l-camphor; 2-phenyl-5-methylbenzoxazol; 2,2'-hydroxy-5-methylphenylbenzotriazol, 2-(2'-hydroxy-5'-t-octylphenyl) benzotriazol, 2-(2'-hydroxy-5'-methylphenylbenzotriazol; dibenzalazine; dianisoylmethane; 4-methoxy-4'-t-butyldibenzoylmethane; 5-(3,3-dimethyl-2-norbornylidene)-3-pentane-2-one; dimorpholinopyridazinone; 2-ethylhexyl 2-cyano-3,3-diphenylacrylate; 2,4-bis-{[4-(2-ethylhexyloxy)-2-hydroxy]-phenyl}-6-(4-methoxyphenyl)-(1,3,5)-triazine, and the like.

Examples of the metal ion sequestrant may include 1-hydroxyethane-1, 1-diphosphonic acid, 1-hydroxyethane, 1-diphosphonic acid 4Na salt, disodium edetate, trisodium edetate, tetrasodium edetate, sodium citrate, sodium polyphosphate, sodium metaphosphate, gluconic acid, phosphoric acid, citric acid, ascorbic acid, succinic acid, edetic acid, trisodium hydroxyethyl ethylenediamine triacetate, and the like.

Examples of the amino acid may include neutral amino acid (such as threonine, cysteine, etc); basic amino acid (such as hydroxylysine, etc) and the like. Examples of the amino acid derivative may include sodium acyl sarcosinate (sodium lauroyl sarcosinate), acyl glutamate, sodium acyl β-alanine, glutathione, pyrrolidone carboxylate, and the like.

Examples of the organic amine may include monoethanolamine, diethanolamine, triethanolamine, morpholine, triisopropanolamine, 2-amino-2-methyl-1,3-propanediol, 2-amino-2-methyl-1-propanol, and the like.

Examples of the polymer emulsion may include acrylic resin emulsion, ethyl polyacrylate emulsion, solution of acrylic resin, polyacrylalkylester emulsion, polyvinyl acetate resin emulsion, natural rubber latex, and the like.

Examples of the pH modifier may include buffer such as lactic acid-sodium lactate, citric acid-sodium citrate, succinic acid-sodium succinate, and the like.

Examples of the vitamins may include vitamine A, B1, B2, B6, C, E and derivatives thereof, pantothenic acid and derivatives thereof, biotin, and the like.

Examples of the anti-oxidant may include tocopherols, dibutyl hydroxy toluene, butyl hydroxy anisole, and gallic acid esters, and the like.

Examples of the anti-oxidant aid may include phosphoric acid, citric acid, ascorbic acid, maleic acid, malonic acid, succinic acid, fumaric acid, cephalin, hexamethaphosphate, phytic acid, ethylenediaminetetraacetic acid, and the like.

Examples of other containable compositions may include an antiseptic agent (such as ethylparaben, butylparaben, chlorphenesin, 2-phenoxyethanol, etc); antiphlogistic (such as glycyrrhizinic acid derivatives, glycyrrhetic acid derivatives, salicylic acid derivatives, hinokitiol, zinc oxide, allantoin, etc); a skin-whitening agent (such as placental extract, saxifrage extract, arbutin, etc); various extracts (such as phellodendron bark (cork tree bark), coptis rhizome, lithospermum, peony, swertia herb, birch, sage, loquat, carrot, aloe, mallow, iris, grape, coix seed, sponge gourd, lily, saffron, cnidium rhizome, ginger, hypericum, restharrow, garlic, red pepper, citrus unshiu, Japanese angelica, seaweed, etc); an activator (such as royal jelly, photosenstizer, cholesterol derivatives, etc); a blood circulation promotion agent (such as nonylic acid vanillylamide, nicotine acid benzyl ester, nicotine acid β-butoxyethyl ester, capsaicin, zingerone, cantharides tincture, ichthammol, tannic acid, α-borneol, tocopheryl nicotinate, meso-inositol hexanicotinate, cyclandelate, cinnarizine, tolazoline, acetylcholine, verapamil, cepharanthine, γ-oryzanol, etc); an antiseborrheric agent, (such as sulfur, thianthl, etc); an anti-inflammatory agent (such as tranexamic acid, thiotaurine, hypotaurine, etc), and the like.

The composition of the present disclosure further may include, as necessary, caffeine, tannin, verapamil, tranexamic acid and derivatives thereof; various crude drug extracts such as licorice, Chinese quince, Pyrola japonica and the like; drugs such as tocopherol acetate, glycyrrhetinic acid, glycyrrhizic acid and derivatives thereof, or salts thereof; skin-whitening agents such as vitamin C, magnesium ascorbyl phosphate, ascorbic acid glucoside, arbutin, kojic acid and the like; amino acids such as arginine and lysine and the like and derivatives thereof.

A method for producing the cleanser composition of the present disclosure will be described. The cleanser composition of the present disclosure can be prepared by any generally known method, without being limited to a specific method. For example, the cleanser composition can be prepared by mixing each of the aforementioned components.

There may be cases where it is difficult, or utterly impractical, to directly define the cleanser composition of the present disclosure based on the composition, structure, configuration, etc., thereof. In such circumstances, it should be permissible to define the cleanser composition of the present disclosure according to methods for producing the same.

EXAMPLES

Cleanser compositions and cleansing products of the present disclosure will be described below by way of examples. Note, however, that the cleanser composition of the present disclosure is not limited to the following examples. The following Examples describe examples wherein the cleanser compositions according to the respective Test Examples are applied to cleansing of a cosmetic, but the composition of the present disclosure is not limited to use for cosmetics. The content by percentage of each of the components shown in the Tables is in terms of percent by mass (mass %).

Test Examples 1 to 4

Cleanser compositions were prepared, to verify whether or not a sponge phase was formed. In Test Examples 1, compositions were prepared by varying the amount of cosurfactants (Components (B)) while keeping the amount of nonionic surfactants (Components (A)) constant, and the electric conductivity of each composition was measured to verify whether or not a sponge phase was formed. Tables 1 and 2 show the compositional make-up and measurement results of the respective Test Examples 1. FIG. 1 shows a graph showing the change in electric conductivity against the content by percentage of the cosurfactants in Test Examples 1. Also in Test Examples 2 to 4, whether or not a sponge phase was formed was verified in the same manner. Tables 3 to 5 show the compositional make-up and measurement results of the respective Test Examples 2 to 4. The evaluation criteria regarding the formation of a sponge phase, as shown in Tables 1 to 5, are as described below.

The HLB of each of the nonionic surfactants used in the following Test Examples is as follows.

(A1) PEG-60 glyceryl isostearate: HLB 16
(A2) PEG-20 glyceryl triisostearate: HLB 8
(A3) PEG-8 glyceryl isostearate: HLB 10
(A4) PEG-7 glyceryl cocoate: HLB 13
(A5) PEG-15 glyceryl isostearate: HLB 12

Electric Conductivity Measurement:

The electric conductivity of each composition was measured at 25° C. with HORIBA ES-71 from Horiba, Ltd.

Formation of Sponge Phase:

A: Formation of a sponge phase was verified;
B: Formation of a sponge phase could not be verified.

Cleansability:

Ten expert panelists, having oil-based makeup on their face, applied each cleanser composition of the respective Test Examples to their face and gently massaged the composition with the hand at a constant force and speed for a given number of times to make it blend with the makeup, and then rinsed the composition off with water or lukewarm water. Thereafter, cleansability was evaluated according to the following criterion.

Evaluation Criterion:

A: 9 or more panelists found that the oil-based makeup could be completely cleansed off;
B: 7 to 8 panelists found that the oil-based makeup could be completely cleansed off;
C: 4 to 6 panelists found that the oil-based makeup could be completely cleansed off;
D: 3 or fewer panelists found that the oil-based makeup could be completely cleansed off.

Appearance:

The appearance (transparency) of each cleanser composition was evaluated according to the following criterion.

A: Transparent;
B: Translucent;
C: Opaque.

FIG. 1 shows that, in Test Examples 1 wherein a plurality of nonionic surfactants having different HLBs were added, a drop in electric conductivity was verified when the amount of cosurfactants added became 0.5% by mass or greater. It is thought that the electric conductivity dropped because a bilayer membrane of surfactants was formed and water was blocked. Stated differently, the drop in electric conductivity is thought to be caused by the formation of a sponge phase. This shows that a sponge phase can be formed by using nonionic surfactants, even without using an ionic surfactant. It was also observed that, with an increase in the amount of cosurfactants, the rating regarding cleansability tended to improve. In Test Examples 1, a sponge phase was formed when the amount of cosurfactants was from 0.1 to 1 part by mass relative to 1 part by mass of nonionic surfactants.

It was possible to verify the formation of a sponge phase in Test Examples 1 wherein ethylhexylglycerin and polyglyceryl-2 laurate were used as cosurfactants. Further, it was possible to verify the formation of a sponge phase also in Test Examples 2 to 4 wherein ethylhexylglycerin was used singly as a cosurfactant. Further, it was possible to verify the formation of a sponge phase also in Test Examples 6 and 7 (described below) wherein polyglyceryl-2 caprate was used as a cosurfactant. These results suggest that alkylglycerols and glycerin fatty acid esters (polyglycerin fatty acid esters) function as a cosurfactant for forming a sponge phase.

In Test Examples 2 to 4, the weighted average HLB of the nonionic surfactants was varied by varying the ratio between PEG-60 glyceryl isostearate (HLB: 16) and PEG-20 glyceryl triisostearate (HLB:8). In all of Test Examples 2 to 4, it was possible to verify the formation of a sponge phase. These results show that, in a composition containing a plurality of nonionic surfactants, a sponge phase can be formed at least when the weighted average HLB is from 10 to 18, preferably from 12 to 16.

The compositions in which a sponge phase was formed all had favorable cleansability. Particularly, when comparing Test Examples 1-1 to 1-2, in which no sponge phase was formed, and Test Examples 1-3 to 1-5, in which a sponge phase was formed, it was found that, even if the amount of nonionic surfactants was the same, the rating regarding cleansability improved significantly when a sponge phase was formed. This suggests that a sponge phase has better cleansability than other phases/states.

The compositions of Test Examples 1 to 4 were all transparent, including translucent.

TABLE 1

| Test Example | 1-1 | 1-2 | 1-3 | 1-4 | 1-5 |
|---|---|---|---|---|---|
| (A1) PEG-60 glyceryl isostearate | 2.1 | 2.1 | 2.1 | 2.1 | 2.1 |
| (A2) PEG-20 glyceryl triisostearate | 0.9 | 0.9 | 0.9 | 0.9 | 0.9 |
| (B) Ethylhexylglycerin | 0 | 0.10 | 0.21 | 0.31 | 0.42 |
| (B) Polyglyceryl-2 laurate | 0 | 0.15 | 0.29 | 0.44 | 0.58 |
| Ion-exchanged water | Balance | Balance | Balance | Balance | Balance |
| Total | 100 | 100 | 100 | 100 | 100 |
| Weighted average HLB | 13.6 | 13.6 | 13.6 | 13.6 | 13.6 |
| (B)/(A) | 0 | 0.083 | 0.17 | 0.25 | 0.33 |
| Electric conductivity (µs) | 22.1 | 23.2 | 24.2 | 22.7 | 22.3 |
| Formation of sponge phase | B | B | A | A | A |
| Cleansability | D | D | B | B | A |
| Appearance | A | A | A | A | B |

TABLE 2

| Test Example | 1-6 | 1-7 | 1-8 | 1-9 | 1-10 |
|---|---|---|---|---|---|
| (A1) PEG-60 glyceryl isostearate | 2.1 | 2.1 | 2.1 | 2.1 | 2.1 |

TABLE 2-continued

| Test Example | 1-6 | 1-7 | 1-8 | 1-9 | 1-10 |
|---|---|---|---|---|---|
| (A2) PEG-20 glyceryl triisostearate | 0.9 | 0.9 | 0.9 | 0.9 | 0.9 |
| (B) Ethylhexylglycerin | 0.63 | 0.73 | 0.83 | 0.94 | 1.04 |
| (B) Polyglyceryl-2 laurate | 0.88 | 1.02 | 1.17 | 1.31 | 1.46 |
| Ion-exchanged water | Balance | Balance | Balance | Balance | Balance |
| Total | 100 | 100 | 100 | 100 | 100 |
| Weighted average HLB | 13.6 | 13.6 | 13.6 | 13.6 | 13.6 |
| (B)/(A) | 0.50 | 0.58 | 0.67 | 0.75 | 0.83 |
| Electric conductivity (µs) | 20.1 | 18.3 | 18.5 | 16.6 | 15.8 |
| Formation of sponge phase | A | A | A | A | A |
| Cleansability | A | A | A | A | A |
| Appearance | B | B | B | B | B |

TABLE 3

| Test Example | 2-1 | 2-2 | 2-3 | 2-4 |
|---|---|---|---|---|
| (A1) PEG-60 glyceryl isostearate | 2.4 | 2.4 | 2.4 | 2.4 |
| (A2) PEG-20 glyceryl triisostearate | 0.6 | 0.6 | 0.6 | 0.6 |
| (B) Ethylhexylglycerin | 1 | 1.5 | 1.75 | 2 |
| Ion-exchanged water | Balance | Balance | Balance | Balance |
| Total | 100 | 100 | 100 | 100 |
| Weighted average HLB | 14.4 | 14.4 | 14.4 | 14.4 |
| (B)/(A) | 0.33 | 0.50 | 0.58 | 0.67 |
| Formation of sponge phase | A | A | A | A |
| Cleansability | A | A | A | A |
| Appearance | A | B | B | B |

TABLE 4

| Test Example | 3-1 | 3-2 | 3-3 | 3-4 |
|---|---|---|---|---|
| (A1) PEG-60 glyceryl isostearate | 2.1 | 2.1 | 2.1 | 2.1 |
| (A2) PEG-20 glyceryl triisostearate | 0.9 | 0.9 | 0.9 | 0.9 |
| (B) Ethylhexylglycerin | 0.75 | 1 | 1.5 | 1.75 |
| Ion-exchanged water | Balance | Balance | Balance | Balance |
| Total | 100 | 100 | 100 | 100 |
| Weighted average HLB | 13.6 | 13.6 | 13.6 | 13.6 |
| (B)/(A) | 0.25 | 0.33 | 0.50 | 0.58 |
| Formation of sponge phase | A | A | A | A |
| Cleansability | A | A | A | A |
| Appearance | B | B | B | B |

TABLE 5

| Test Example | 4-1 | 4-2 | 4-3 | 4-4 |
|---|---|---|---|---|
| (A1) PEG-60 glyceryl isostearate | 1.8 | 1.8 | 1.8 | 1.8 |
| (A2) PEG-20 glyceryl triisostearate | 1.2 | 1.2 | 1.2 | 1.2 |
| (B) Ethylhexylglycerin | 0.5 | 0.75 | 1 | 1.5 |
| Ion-exchanged water | Balance | Balance | Balance | Balance |
| Total | 100 | 100 | 100 | 100 |
| Weighted average HLB | 12.8 | 12.8 | 12.8 | 12.8 |
| (B)/(A) | 0.17 | 0.25 | 0.33 | 0.50 |
| Formation of sponge phase | A | A | A | A |
| Cleansability | A | A | A | A |
| Appearance | A | B | B | B |

Test Examples 5 to 7

Cleanser compositions were prepared in the same manner as in Test Examples 1 to 4, to verify whether or not a sponge phase was formed. Tables 6 to 8 show the compositional make-up and results of the respective Test Examples 5 to 7. Formation of a sponge phase was verified by measuring electric conductivity.

In Test Examples 5, the types and amounts of nonionic surfactants were varied. In all of the compositions, it was possible to verify the formation of a sponge phase. This suggests that a sponge phase can be formed if at least a polyoxyalkylene glycerin fatty acid ester is used as the nonionic surfactant.

Also in Test Examples 6 and 7 wherein the types and content percentages of cosurfactants were varied, it was possible to verify the formation of a sponge phase.

This, together with the aforementioned Test Examples, suggests that, in a system including a plurality of nonionic surfactants having different HLBs, it is preferred that the amount of cosurfactant(s) is preferably 0.3% by mass or greater, more preferably 0.5% by mass or greater. The result also suggests that the amount of cosurfactant(s) is preferably 0.1 parts by mass or greater relative to 1 part by mass of nonionic surfactants.

The cleansability and appearance of the compositions of Test Examples 5 to 7 were all favorable.

TABLE 6

| Test Example | 5-1 | 5-2 | 5-3 |
|---|---|---|---|
| (A1) PEG-60 glyceryl isostearate | 2.5 | 2.5 | 2.5 |
| (A2) PEG-20 glyceryl triisostearate | 0.9 | 0.9 | — |
| (A3) PEG-8 glyceryl isostearate | — | — | 0.13 |
| (B) Ethylhexylglycerin | 0.5 | 0.5 | 0.5 |
| (B) Polyglyceryl-2 laurate | 0.7 | 0.7 | — |
| Glycerin | — | 2 | 2 |
| Dipropylene glycol | 6 | 6 | 6 |
| Methylparaben | q.s. | — | — |
| Phenoxyethanol | — | q.s. | q.s. |
| Citric acid | — | q.s. | q.s. |
| Sodium citrate | — | q.s. | q.s. |
| EDTA-2Na•2H$_2$O | q.s. | q.s. | q.s. |
| Perfume | — | q.s. | q.s. |
| Ion-exchanged water | Balance | Balance | Balance |
| Total | 100 | 100 | 100 |
| Weighted average HLB | 13.9 | 13.9 | 15.7 |
| (B)/(A) | 0.35 | 0.35 | 0.19 |
| Formation of sponge phase | A | A | A |
| Cleansability | A | A | B |
| Appearance | B | A | A |

TABLE 7

| Test Example | 6-1 | 6-2 | 6-3 | 6-4 |
|---|---|---|---|---|
| (A1) PEG-60 glyceryl isostearate | 2.5 | 2.5 | 2.5 | 2.5 |
| (A3) PEG-8 glyceryl isostearate | 0.13 | 0.13 | 0.13 | 0.13 |
| (B) Ethylhexylglycerin | 0.5 | 0.5 | 0.5 | 0.5 |
| (B) Polyglyceryl-2 caprate | 0.1 | 0.2 | 0.3 | 0.4 |
| Glycerin | 2 | 2 | 2 | 2 |
| Dipropylene glycol | 6 | 6 | 6 | 6 |
| Phenoxyethanol | q.s. | q.s. | q.s. | q.s. |
| Citric acid | q.s. | q.s. | q.s. | q.s. |
| Sodium citrate | q.s. | q.s. | q.s. | q.s. |
| EDTA-2Na•2H$_2$O | q.s. | q.s. | q.s. | q.s. |
| Perfume | q.s. | q.s. | q.s. | q.s. |
| Ion-exchanged water | Balance | Balance | Balance | Balance |
| Total | 100 | 100 | 100 | 100 |
| Weighted average HLB | 15.7 | 15.7 | 15.7 | 15.7 |
| (B)/(A) | 0.23 | 0.27 | 0.30 | 0.34 |
| Formation of sponge phase | A | A | A | A |
| Cleansability | B | B | B | A |
| Appearance | A | A | A | A |

TABLE 8

| Test Example | 7-1 | 7-2 | 7-3 | 7-4 | 7-5 |
|---|---|---|---|---|---|
| (A1) PEG-60 glyceryl isostearate | 2.5 | 2.5 | 2.5 | 2.5 | 2.5 |
| (A3) PEG-8 glyceryl isostearate | 0.13 | 0.13 | 0.13 | 0.13 | 0.13 |
| (A4) PEG-7 glyceryl cocoate | 0.1 | 0.2 | 0.3 | 0.4 | 0.4 |
| (B) Ethylhexylglycerin | 0.5 | 0.5 | 0.5 | 0.5 | 0.5 |
| (B) Polyglyceryl-2 caprate | — | — | — | — | 0.5 |
| Dipropylene glycol | 6 | 6 | 6 | 6 | 6 |
| Phenoxyethanol | q.s. | q.s. | q.s. | q.s. | q.s. |
| Citric acid | q.s. | q.s. | q.s. | q.s. | q.s. |
| Sodium citrate | q.s. | q.s. | q.s. | q.s. | q.s. |
| EDTA-2Na•2H$_2$O | q.s. | q.s. | q.s. | q.s. | q.s. |
| Perfume | q.s. | q.s. | q.s. | q.s. | q.s. |
| Ion-exchanged water | Balance | Balance | Balance | Balance | Balance |
| Total | 100 | 100 | 100 | 100 | 100 |
| Weighted average HLB | 15.6 | 15.5 | 15.4 | 15.3 | 15.3 |
| (B)/(A) | 0.18 | 0.18 | 0.17 | 0.17 | 0.33 |
| Formation of sponge phase | A | A | A | A | A |
| Cleansability | B | B | B | A | A |
| Appearance | A | A | A | A | A |

Test Example 8

Cleanser compositions were prepared in the same manner as in Test Examples 1 to 4, to verify whether or not a sponge phase was formed. Tables 9 to 11 show the compositional make-up and results of Test Examples 8. Formation of a sponge phase was verified by measuring electric conductivity. In Tables 9 to 11, EO is an acronym of ethylene oxide, and PO is an acronym of propylene oxide.

In Test Examples 8-1 to 8-5 wherein the content by percentage of the cosurfactant was varied in a system including a plurality of nonionic surfactants having different HLBs, it was possible to verify the formation of a sponge phase. Also, in Test Examples 8-6 to 8-10 wherein the content by percentage of the nonionic surfactants was varied, it was possible to verify the formation of a sponge phase. In contrast, in Test Examples 8-11 to 8-13 wherein no nonionic surfactant was added or only one type of nonionic surfactant was added, formation of a sponge phase could not be verified. Note, however, that in later-described Test Examples 9 to 13, formation of a sponge phase was possible, even though only one type of nonionic surfactant was added. These results suggest that, compared to cases where only one type of nonionic surfactant is used, the use of a plurality of nonionic surfactants having different HLBs allows a sponge phase to be formed even in cases where the content by percentage of the cosurfactant is low.

In Test Examples 8-11, 8-12, and 8-14 wherein no cosurfactant was added, formation of a sponge phase could not be verified. Particularly, in Test Example 8-14, no sponge phase was verified, even though two types of nonionic surfactants were added. These results suggest that, in a system including a plurality of nonionic surfactants having different HLBs, the amount of cosurfactant preferable for forming a sponge phase is preferably 0.10% by mass or greater.

As in Test Examples 1, in Test Examples 8-11 to 8-14 wherein no sponge phase was formed, the rating regarding cleansability was poorer compared to Test Examples 8-1 to 8-10 wherein a sponge phase was formed.

TABLE 9

| Test Example | 8-1 | 8-2 | 8-3 | 8-4 | 8-5 |
|---|---|---|---|---|---|
| (A1) PEG-60 glyceryl isostearate | 2 | 2 | 2 | 2 | 2 |
| (A3) PEG-8 glyceryl isostearate | 0.1 | 0.1 | 0.1 | 0.1 | 0.1 |
| (B) Ethylhexylglycerin | 0.3 | 0.4 | 0.5 | 0.4 | 0.4 |
| $CH_3O[(EO)_{14}(PO)_7]CH_3$*[1] | 2 | 2 | 2 | 1 | 3 |
| Glycerin | 2 | 2 | 2 | 2 | 2 |
| Dipropylene glycol | 4 | 4 | 4 | 4 | 4 |
| 1,3-Butylene glycol | 8 | 8 | 8 | 8 | 8 |
| Sodium polyacrylate | 0.003 | 0.003 | 0.003 | 0.003 | 0.003 |
| Phenoxyethanol | q.s. | q.s. | q.s. | q.s. | q.s. |
| Citric acid | q.s. | q.s. | q.s. | q.s. | q.s. |
| Sodium citrate | q.s. | q.s. | q.s. | q.s. | q.s. |
| EDTA-2Na•2H$_2$O | q.s. | q.s. | q.s. | q.s. | q.s. |
| Perfume | q.s. | q.s. | q.s. | q.s. | q.s. |
| Ion-exchanged water | Balance | Balance | Balance | Balance | Balance |
| Total | 100 | 100 | 100 | 100 | 100 |
| Weighted average HLB | 15.7 | 15.7 | 15.7 | 15.7 | 15.7 |
| (B)/(A) | 0.14 | 0.19 | 0.24 | 0.19 | 0.19 |
| Formation of sponge phase | A | A | A | A | A |
| Cleansability | B | B | B | B | B |
| Appearance | A | A | A | A | A |

*[1]Random copolymer

TABLE 10

| Test Example | 8-6 | 8-7 | 8-8 | 8-9 | 8-10 |
|---|---|---|---|---|---|
| (A1) PEG-60 glyceryl isostearate | 2 | 1.5 | 2 | 2.5 | 1.5 |
| (A3) PEG-8 glyceryl isostearate | 0.05 | 0.1 | 0.13 | 0.1 | 0.05 |
| (B) Ethylhexylglycerin | 0.4 | 0.4 | 0.4 | 0.4 | 0.3 |
| $CH_3O[(EO)_{14}(PO)_7]CH_3$*[1] | 2 | 2 | 2 | 2 | 2 |
| Glycerin | 2 | 2 | 2 | 2 | 2 |
| Dipropylene glycol | 4 | 4 | 4 | 4 | 4 |
| 1,3-Butylene glycol | 8 | 8 | 8 | 8 | 8 |
| Sodium polyacrylate | 0.003 | 0.003 | 0.003 | 0.003 | 0.003 |
| Phenoxyethanol | q.s. | q.s. | q.s. | q.s. | q.s. |
| Citric acid | q.s. | q.s. | q.s. | q.s. | q.s. |
| Sodium citrate | q.s. | q.s. | q.s. | q.s. | q.s. |
| EDTA-2Na•2H$_2$O | q.s. | q.s. | q.s. | q.s. | q.s. |
| Perfume | q.s. | q.s. | q.s. | q.s. | q.s. |
| Ion-exchanged water | Balance | Balance | Balance | Balance | Balance |
| Total | 100 | 100 | 100 | 100 | 100 |
| Weighted average HLB | 15.9 | 15.6 | 15.6 | 15.8 | 15.8 |
| (B)/(A) | 0.20 | 0.25 | 0.19 | 0.15 | 0.19 |
| Formation of sponge phase | A | A | A | A | A |
| Cleansability | B | B | B | B | B |
| Appearance | A | A | A | A | A |

TABLE 11

| Test Example | 8-11 | 8-12 | 8-13 | 8-14 |
|---|---|---|---|---|
| (A1) PEG-60 glyceryl isostearate | 2 | — | — | 2 |
| (A3) PEG-8 glyceryl isostearate | — | 0.1 | — | 0.1 |
| (B) Ethylhexylglycerin | — | — | 0.4 | — |
| $CH_3O[(EO)_{14}(PO)_7]CH_3$*[1] | 2 | 2 | 2 | 2 |
| Glycerin | 2 | 2 | 2 | 2 |
| Dipropylene glycol | 4 | 4 | 4 | 4 |
| 1,3-Butylene glycol | 8 | 8 | 8 | 8 |
| Sodium polyacrylate | 0.003 | 0.003 | 0.003 | 0.003 |
| Phenoxyethanol | q.s. | q.s. | q.s. | q.s. |
| Citric acid | q.s. | q.s. | q.s. | q.s. |
| Sodium citrate | q.s. | q.s. | q.s. | q.s. |
| EDTA-2Na•2H$_2$O | q.s. | q.s. | q.s. | q.s. |
| Perfume | q.s. | q.s. | q.s. | q.s. |
| Ion-exchanged water | Balance | Balance | Balance | Balance |
| Total | 100 | 100 | 100 | 100 |
| Weighted average HLB | 16 | 10 | — | 15.7 |
| (B)/(A) | 0 | 0 | — | 0 |
| Formation of sponge phase | B | B | B | B |

TABLE 11-continued

| Test Example | 8-11 | 8-12 | 8-13 | 8-14 |
|---|---|---|---|---|
| Cleansability | D | D | D | D |
| Appearance | A | A | A | A |

Test Examples 91 to 11

The aforementioned Test Examples employed a plurality of nonionic surfactants. Tests were conducted to verify whether a sponge phase could be formed even with one type of nonionic surfactant. In Test Examples 9 to 11, the content by percentage of the cosurfactant was varied while keeping the content by percentage of the nonionic surfactant constant. Tables 12 to 14 show the compositional make-up and results. Formation of a sponge phase was verified by measuring electric conductivity.

It was possible to verify that a sponge phase can be formed even with one type of nonionic surfactant. It was possible to verify that a sponge phase can be formed if at least a polyoxyalkylene glycerin fatty acid ester is used as the nonionic surfactant. It is thought that, in cases where one type of nonionic surfactant is used, the content of the nonionic surfactant may be 1% by mass or greater relative to the mass of the cleanser composition.

Adding a cosurfactant resulted in a decrease in electric conductivity, and formation of a sponge phase was verified. It was possible to verify that a sponge phase can be formed if at least a glycerin fatty acid ester (polyglycerin fatty acid ester) is used as the cosurfactant. It is thought that the amount of the cosurfactant may be 0.3% by mass or greater relative to the mass of the cleanser composition.

TABLE 12

| Test Example | 9-1 | 9-2 | 9-3 | 9-4 |
|---|---|---|---|---|
| (A4) PEG-7 glyceryl cocoate | 2 | 2 | 2 | 2 |
| (B) Ethylhexylglycerin | 0 | 0.5 | 1 | 2 |
| Ion-exchanged water | Balance | Balance | Balance | Balance |
| Total | 100 | 100 | 100 | 100 |
| (A)HLB | 13 | 13 | 13 | 13 |
| (B)/(A) | 0 | 0.25 | 0.50 | 1 |
| Formation of sponge phase | B | A | A | A |

TABLE 13

| Test Example | 10-1 | 10-2 | 10-3 | 10-4 | 10-5 | 10-6 |
|---|---|---|---|---|---|---|
| (A4) PEG-7 glyceryl cocoate | 2 | 2 | 2 | 2 | 2 | 2 |
| (B) Polyglyceryl-2 caprate | 0 | 0.5 | 1 | 1.5 | 2 | 5 |
| Ion-exchanged water | Balance | Balance | Balance | Balance | Balance | Balance |
| Total | 100 | 100 | 100 | 100 | 100 | 100 |
| (A)HLB | 13 | 13 | 13 | 13 | 13 | 13 |
| (B)/(A) | 0 | 0.25 | 0.50 | 0.75 | 1.0 | 2.5 |
| Formation of sponge phase | B | A | A | A | A | A |

TABLE 14

| Test Example | 11-1 | 11-2 | 11-3 | 11-4 |
|---|---|---|---|---|
| (A5) PEG-15 glyceryl isostearate | 2 | 2 | 2 | 2 |
| (B) Ethylhexylglycerin | 0 | 0.5 | 1 | 2 |
| Ion-exchanged water | Balance | Balance | Balance | Balance |
| Total | 100 | 100 | 100 | 100 |
| (A)HLB | 12 | 12 | 12 | 12 |
| (B)/(A) | 0 | 0.25 | 0.50 | 1 |
| Formation of sponge phase | B | A | A | A |

Test Examples 12 and 13

As in Test Examples 9 to 11, tests were conducted to verify whether or not a sponge phase could be formed using one type of nonionic surfactant. In Test Examples 12 and 13, the content by percentage of the nonionic surfactant and that of the cosurfactant were varied. Tables 15 and 16 show the compositional make-up and results. Formation of a sponge phase was verified by measuring electric conductivity.

In both Test Examples 12 and 13, compositions including the cosurfactant had lower electric conductivity and formation of a sponge phase could be verified, in contrast to compositions not including the cosurfactant. It is thought that the content of the nonionic surfactant may be 50% by mass or less relative to the mass of the cleanser composition. It was also found that the cosurfactant may at least be added to a content of 25% by mass relative to the mass of the cleanser composition.

In Test Examples 9 to 13, which were modes employing one type of nonionic surfactant, a sponge phase was formed when the amount of the cosurfactant was from 0.1 to 3 parts by mass relative to 1 part by mass of the nonionic surfactant.

In Test Examples 9 to 13, which were modes employing one type of nonionic surfactant, it was possible to form a sponge phase by using one of nonionic surfactants respectively having HLBs of from 10 to 14.

TABLE 15

| Test Example | 12-1 | 12-2 | 12-3 | 12-4 | 12-5 |
|---|---|---|---|---|---|
| (A5) PEG-15 glyceryl isostearate | 50 | 45 | 41.25 | 40 | 37.5 |
| (B) Ethylhexylglycerin | 0 | 10 | 17.5 | 20 | 25 |
| Ion-exchanged water | Balance | Balance | Balance | Balance | Balance |
| Total | 100 | 100 | 100 | 100 | 100 |
| (A)HLB | 12 | 12 | 12 | 12 | 12 |
| (B)/(A) | 0 | 0.22 | 0.42 | 0.50 | 0.67 |
| Formation of sponge phase | B | A | A | A | A |

TABLE 16

| Test Example | 13-1 | 13-2 | 13-3 | 13-4 | 13-5 | 13-6 |
|---|---|---|---|---|---|---|
| (A5) PEG-15 glyceryl isostearate | 40 | 36 | 35.2 | 33 | 32 | 30 |
| (B) Ethylhexylglycerin | 0 | 10 | 12 | 17.5 | 20 | 25 |
| Ion-exchanged water | Balance | Balance | Balance | Balance | Balance | Balance |
| Total | 100 | 100 | 100 | 100 | 100 | 100 |
| (A)HLB | 12 | 12 | 12 | 12 | 12 | 12 |
| (B)/(A) | 0 | 0.28 | 034 | 0.53 | 0.63 | 0.83 |
| Formation of sponge phase | B | A | A | A | A | A |

The cleanser composition according to the present invention have been described according to the foregoing embodiments and examples, but the invention is not limited to the foregoing embodiments and examples and may encompass various transformations, modifications, and improvements made to the various disclosed elements (including elements disclosed in the Claims, Description, and Drawings) within the scope of the invention and according to the fundamental technical idea of the present invention. Further, various combinations, substitutions, and selections of the various disclosed elements are possible within the scope of the claims of the invention.

Further issues, objectives, and embodiments (including modifications) of the present invention are revealed also from the entire disclosure of the invention including the Claims.

The numerical ranges disclosed herein are to be construed in such a manner that arbitrary numerical values and ranges falling within the disclosed ranges are treated as being concretely described herein, even where not specifically stated.

Some or all of the foregoing embodiments may be described as in the following additional features, although not limited thereto. The various additional features may be employed in combination with the claim(s) in the Scope of Claims.

{Additional Feature 1}

A method of use, comprising removing a cosmetic with the cleanser composition of the present disclosure.

{Additional Feature 2}

A method of using the cleanser composition of the present disclosure as a leave-on-type or wipe-off-type composition.

INDUSTRIAL APPLICABILITY

The cleanser composition of the present disclosure can suitably be used also for cleansing various products other than the skin.

The invention claimed is:

1. A cleanser composition comprising:
   (A) a nonionic surfactant having a HLB of from 8 to 18; and
   (B) a cosurfactant including at least one selected from the group consisting of alkylglycerols and glycerin fatty acid esters, and
   (C) 70% by mass or greater of water relative to the mass of the cleanser composition, wherein:
   the nonionic surfactant is at least one of PEG-60 glyceryl isostearate, PEG-20 glyceryl triisostearate, PEG-8 glyceryl isostearate, PEG-7 glyceryl cocoate, and PEG-15 glyceryl isostearate,
   wherein:
   a content of the nonionic surfactant is 1% by mass or greater relative to the mass of the cleanser composition,
   a content of the cosurfactant is 0.3% by mass or greater relative to the mass of the cleanser composition;
   a total amount of the cosurfactant is from 0.1 to 0.9 parts by mass relative to 1 part by mass of the nonionic surfactant;
   the nonionic surfactant assembles together in water to form a continuous assembly, and the hydrophilic groups of the continuous assembly retain water to form a sponge phase; and
   a total amount of ionic surfactants is 0.1% by mass or less relative to the mass of the cleanser composition.

2. The cleanser composition according to claim 1, wherein:
   the nonionic surfactant has a HLB of from 10 to 14; and
   a content of the nonionic surfactant is from 1% to 5% by mass relative to the mass of the cleanser composition.

3. A cleanser composition comprising:
   (A) at least two types of nonionic surfactants respectively having different HLBs;
   (B) a cosurfactant including at least one selected from the group consisting of alkylglycerols and glycerin fatty acid esters, and
   (C) 70% by mass or greater of water relative to the mass of the cleanser composition, wherein:
   the nonionic surfactant is at least two of PEG-60 glyceryl isostearate, PEG-20 glyceryl triisostearate, PEG-8 glyceryl isostearate, PEG-7 glyceryl cocoate, and PEG-15 glyceryl isostearate, wherein:
   a content of the nonionic surfactant is 1% by mass or greater relative to the mass of the cleanser composition,
   a content of the cosurfactant is 0.3% by mass or greater relative to the mass of the cleanser composition;
   a total amount of the cosurfactant is from 0.1 to 0.9 parts by mass relative to 1 part by mass of the nonionic surfactants;
   the nonionic surfactants assemble together in water to form a continuous assembly, and the hydrophilic groups of the continuous assembly retain water to form a sponge phase; and
   a total amount of ionic surfactants is 0.1% by mass or less relative to the mass of the cleanser composition.

4. The cleanser composition according to claim 3, wherein the nonionic surfactants have a weighted average HLB of from 10 to 18.

5. The cleanser composition according to claim 3, wherein the nonionic surfactants include:
   a first nonionic surfactant having a HLB of 14 or greater; and
   a second nonionic surfactant having a HLB of from 6 to 13.

6. The cleanser composition according to claim 5, wherein,
   relative to the mass of the cleanser composition,
   a content of the first nonionic surfactant is from 0.5 to 5% by mass, and
   a content of the second nonionic surfactant is from 0.02 to 3% by mass.

7. The cleanser composition according to claim 1, wherein the alkylglycerols are ethylhexylglycerin, and
   the glycerin fatty acid esters are polyglyceryl-2 laurate or polyglyceryl-2 caprate.

8. The cleanser composition according to claim 1, wherein the composition comprises an oily component and a content of the oily component is 1% by mass or less relative to the mass of the cleanser composition.

9. The cleanser composition according to claim 1, wherein the cleanser composition is applicable to cleansing of a cosmetic.

10. The cleanser composition according to claim 1, wherein the cleanser composition is usable as a leave-on-type or wipe-off-type composition.

11. The cleanser composition according to claim 3, wherein the composition comprises an oily component and a content of the oily component is 1% by mass or less relative to the mass of the cleanser composition.

12. The cleanser composition according to claim 3, wherein the alkylglycerols are ethylhexylglycerin, and
   the glycerin fatty acid esters are polyglyceryl-2 laurate or polyglyceryl-2 caprate.

13. The cleanser composition according to claim 3, wherein the cleanser composition is usable as a leave-on-type or wipe-off-type composition.

14. The cleanser composition according to claim 1, wherein substantially no ionic surfactant is contained in the composition.

15. The cleanser composition according to claim 3, wherein substantially no ionic surfactant is contained in the composition.

* * * * *